United States Patent [19]

Meek et al.

[11] Plant 5,028

[45] Apr. 5, 1983

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 304,332

[22] Filed: Sep. 21, 1981

[51] Int. Cl.[3] ..... A01H 5/00

[52] U.S. Cl. ..... Plt./78

[58] Field of Search ..... Plt./78

*Primary Examiner*—James R. Feyrer

*Attorney, Agent, or Firm*—Schwartz, Jeffery, Schwaab, Mack, Blumenthal & Koch

[57] ABSTRACT

A chrysanthemum plant known by the cultivar name Songster and particularly characterized as to uniqueness by the combined characteristics of flat capitulum form; spooned anemone capitulum type; light yellow ray floret color; diameter across face of capitulum ranging from 85 to 100 mm. at maturity; uniform eight week photoperiodic flowering response to short days; medium plant height when grown as a pinched spray pot, and semi-spreading branching pattern.

3 Drawing Figures

The present invention comprises a new and distinct cultivar of *Chrysanthemum morifolium,* Ramat., hereinafter referred to by the cultivar name Songster.

Songster is a product of a planned breeding program which had the objective of creating new chrysanthemum cultivars for pinched spray pot mum programs having spooned anemone capitulum type, yellow or white ray floret color, eight week flowering response, and having the ability to produce commercially acceptable quality in year round programs. Such traits in combination were not present in previously available commercial cultivars.

Songster was originated from a cross made in a controlled breeding program in Salinas, Calif. in 1977. The female parent was Quills, disclosed in U.S. Plant Pat. No. 4,401. The male parent of Songster was an unnamed ivory white spooned anemone seedling originated from a hybridization between Smile and Spindles (both unpatented but commercially available).

Songster was discovered and selected as one flowering plant within the progeny of the stated cross by William E. Duffett on Nov. 17, 1978 in a controlled environment in Salinas, Calif.

The first act of asexual reproduction of Songster was accomplished when vegetative cuttings were taken from the initial selection in February, 1979 in a controlled environment in Salinas, Calif. by a technician working under formulations established and supervised by Jack M. Meek. Horticultural examination of selected units initiated Aug. 22, 1979 has demonstrated that the combination of characteristics as herein disclosed for Songster are firmly fixed and are retained through successive generations of asexual reproduction.

Songster has not been observed under all environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Songster which in combination distinguish this chrysanthemum as a new and distinct cultivar:

(1) flat capitulum form;

(2) spooned anemone capitulum type;

(3) light yellow ray floret color, with rapid color oxidation;

(4) diameter across face of capitulum ranging from 85 to 100 mm. at maturity;

(5) uniform eight week photoperiodic flowering response to short days;

(6) medium plant height (requiring 1–2 long day weeks prior to pinch and short days, and one application 2500 ppm B-9 SP 14 to 21 days after the beginning of short days to attain a flowered plant height of 25 to 35 cm.), and (7) semi-spreading branching pattern.

The accompanying photographic drawings show typical inflorescence and foliage characteristics of Songster, with the colors being as nearly true as possible with illustrations of this type. Sheet 1 is a color photograph of a flowering plant of Songster, Sheet 2 is a black and white photograph showing three views of the inflorescence of Songster. Sheet 3 is a black and white photograph showing the foliage of Songster at three stages of growth.

Of the many commercial cultivars known to the present inventors, the most similar in comparison to Songster is Spice, disclosed in U.S. Plant Pat. No. 3,777. Reference is made to attached Chart A which compares certain characteristics of Songster to those same characteristics of Spice. General comparisons are as follows:

(1) In comparison to Spice, Songster has light yellow ray floret color with more rapid color oxidation, different capitulum type, and larger diameter across face of the capitulum. The capitulum form, branching pattern, plant height and flowering response period of Songster are similar to those same characteristics of Spice.

In the following description, color references are made to A Limit Color Cascade by the Munsell Company, 1972 edition. The color values were determined between 8:00 and 8:30 A.M. on Oct. 6, 1980 under 150 foot-candle light intensity at Salinas, Calif.

Classification:

*Botanical.*—*Chrysanthemum morifolium,* Ramat., cv Songster.

*Commercial.*—Pinched spray spooned anemone pot mum.

I. INFLORESCENCE

A. Capitulum:

*Form.*—Flat.

*Type.*—Spooned anemone. Tubular ray florets with little to no flair at petal tip; elongated disc floret, typical anemone.

B. Corolla of ray florets:

*General tonality from a distance of three meters.*—Light yellow; 26-2.

*Color (adaxial).*—Approximately 26-4 oxidizing rapidly to 26-2.

*Persistence.*—Resists shatter.

C. Corolla of disc florets:

*Color (immature).*—Approximately 21-12 to 21-11.

*Color (mature).*—Approximately 26-6.

D. Reproductive organs:

*Androecium.*—Present in disc florets only; slight pollen.

*Gynoecium.*—Present in both ray and disc florets.

II. PLANT

A. General appearance:

*Height.*—Medium; requiring 1-2 long day weeks prior to pinch and the beginning of short days, with 1 application 2500 ppm B-9 SP applied 14 to 21 days after the beginning of short days to attain a height of 25 to 35 cm.

*Branching pattern.*—Free breaking and semi-spreading.

B. Foliage:

*Color (abaxial).*—Approximately 20-15.

*Color (adaxial).*—Approximately 20-15 overlaid with white.

*Shape.*—Moderately lobed and serrated.

CHART A

COMPARISON OF SONGSTER AND SPICE

| CULTIVAR | RAY FLORET COLOR | CAPITULUM FORM AND TYPE | BRANCHING PATTERN |
|---|---|---|---|
| Songster | Light Yellow Oxidizing Rapidly | Flat Spooned Anemone | Semi-Spreading |
| Spice | Dark Yellow with excellent color retention | Flat spooned Daisy | Semi-Spreading |

| CULTIVAR | DIAMETER ACROSS FACE OF CAPITULUM | PLANT HEIGHT | FLOWERING RESPONSE PERIOD |
|---|---|---|---|
| Songster | 85 to 100 mm. | Medium | 8 Week |
| Spice | 75 to 80 mm. | Medium | 8 Week |

COMPARISONS MADE OF PLANTS GROWN AS PINCHED SPRAY POTS IN SALINAS, CALIFORNIA

We claim:

1. A new and distinct cultivar of *Chrysanthemum morifolium*, Ramat., plant known by the cultivar name of Songster, as described and illustrated, and particularly characterized as to uniqueness by the combined characteristics of flat capitulum form; spooned anemone capitulum type; light yellow ray floret color, with rapid color oxidation; diameter across face of capitulum ranging from 85 to 100 mm. at maturity; uniform eight week flowering response; medium plant height, and semi-spreading branching pattern.

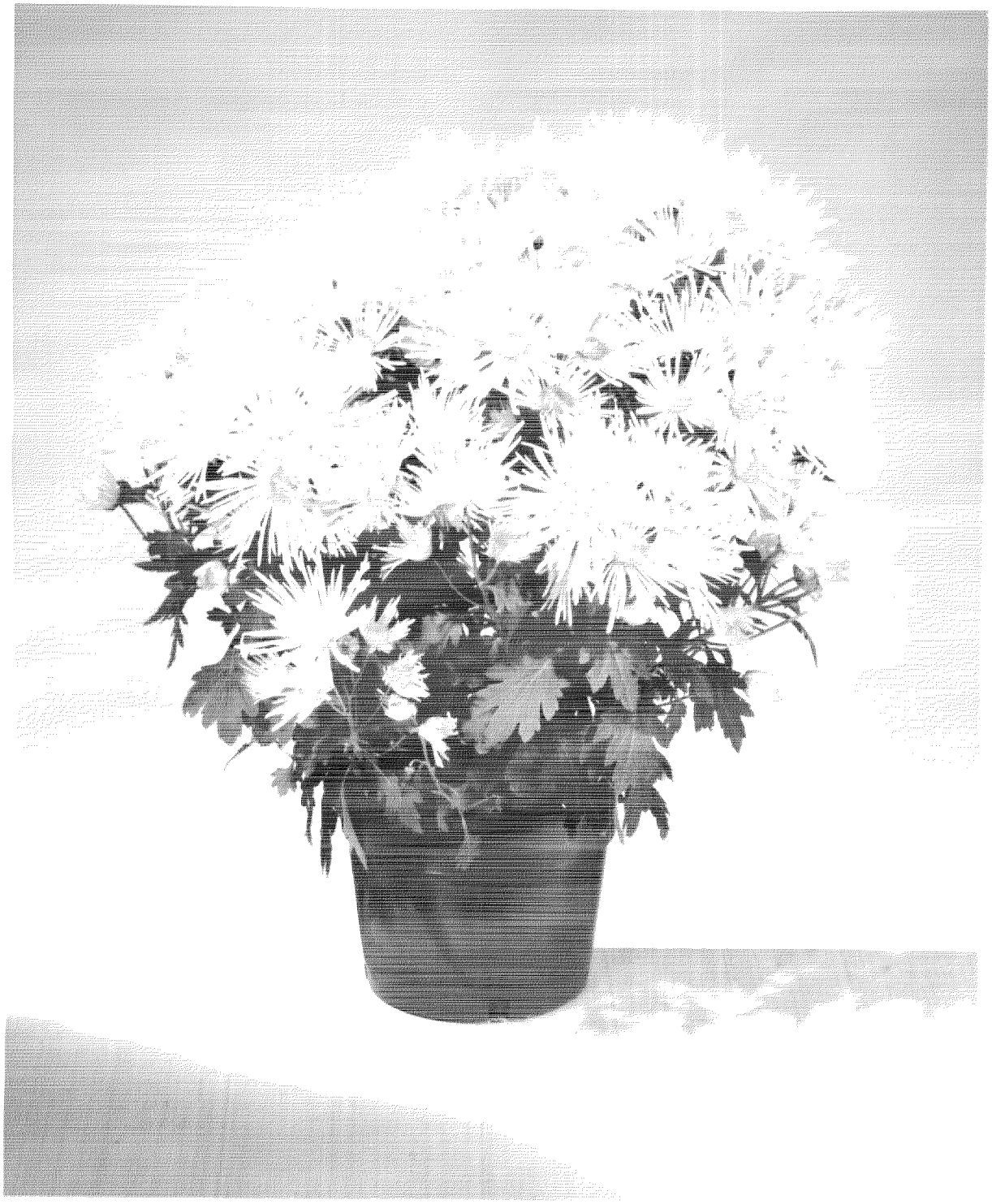

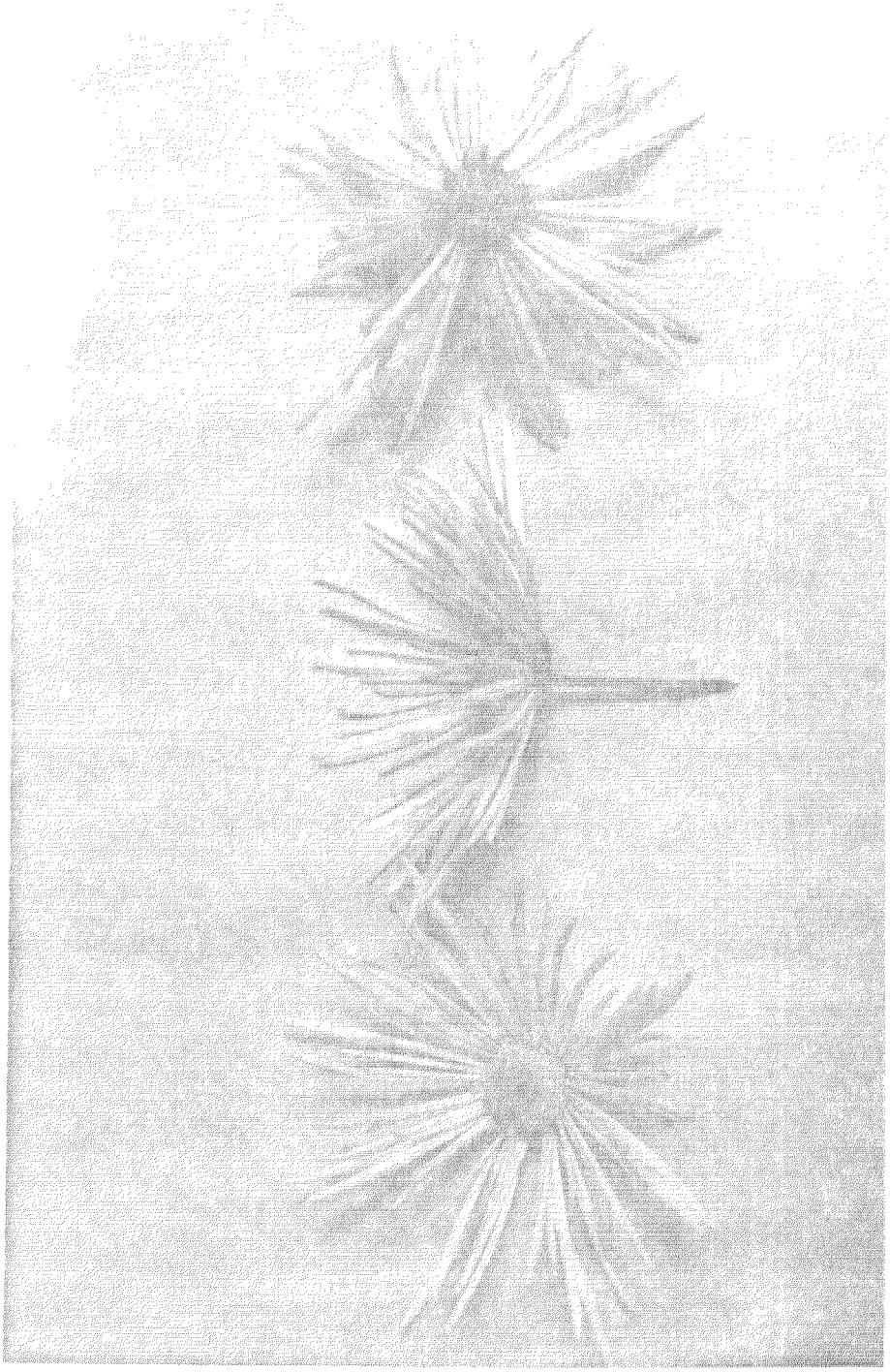

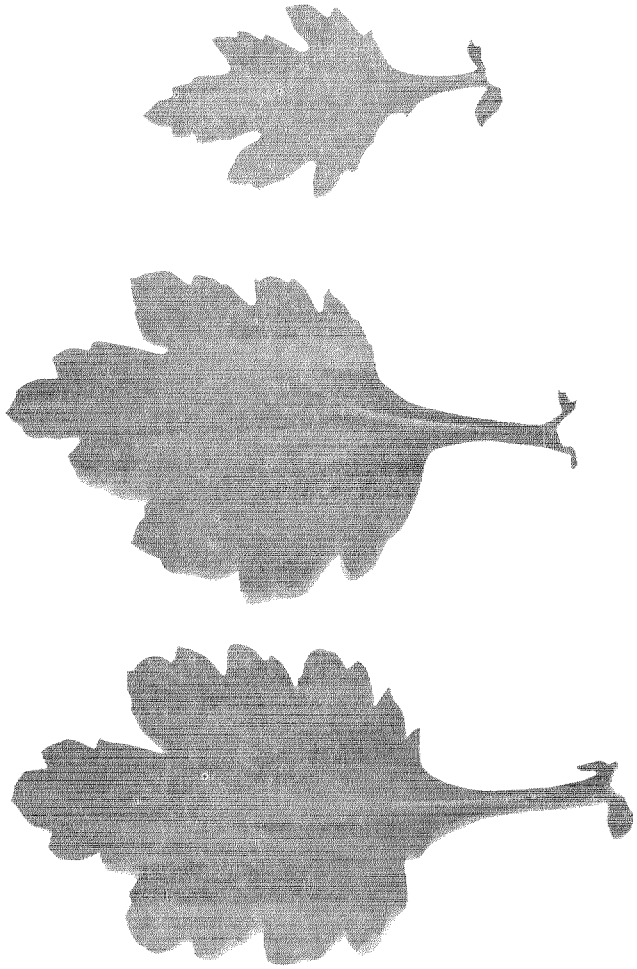

* * * * *